(12) United States Patent
Panetz (10) Patent No.: US 8,808,644 B2
(45) Date of Patent: Aug. 19, 2014

(54) METHODS FOR DISPENSING FLUIDS INTO MICROPLATES UTILIZING MICROWELL COVERS

(75) Inventor: Allen I. Panetz, Edgewood, NY (US)

(73) Assignee: Biochemical Diagnostics, Inc., Edgewood, NY (US)

( * ) Notice: Subject to any disclaimer, the term of this patent is extended or adjusted under 35 U.S.C. 154(b) by 0 days.

(21) Appl. No.: 13/589,869

(22) Filed: Aug. 20, 2012

(65) Prior Publication Data
US 2014/0048168 A1    Feb. 20, 2014

(51) Int. Cl.
  *B01L 3/02* (2006.01)
  *B01L 99/00* (2010.01)
  *B65B 1/04* (2006.01)

(52) U.S. Cl.
  USPC ........... 422/509; 422/569; 141/339; 141/370; 73/864.01; 73/864.14; 73/864.17

(58) Field of Classification Search
  USPC ........................... 422/569; 222/182, 279, 111
  See application file for complete search history.

(56) References Cited

U.S. PATENT DOCUMENTS

| | | | |
|---|---|---|---|
| 2,549,013 A * | 4/1951 | Robles et al. | 220/4.31 |
| 2,604,249 A | 7/1952 | Gorham | |
| 4,191,234 A | 3/1980 | Rubin et al. | |
| 4,349,632 A | 9/1982 | Lyman et al. | |
| 4,919,894 A * | 4/1990 | Daniel | 422/561 |
| 4,988,618 A * | 1/1991 | Li et al. | 435/6.13 |
| 5,484,731 A | 1/1996 | Stevens | |
| 6,106,783 A * | 8/2000 | Gamble | 422/553 |
| 6,135,406 A * | 10/2000 | DeStefano, Jr. | 248/309.1 |
| 6,360,792 B1 | 3/2002 | Ganz et al. | |
| 6,463,969 B1 | 10/2002 | Devlin, Sr. | |
| 7,208,125 B1 * | 4/2007 | Dong | 422/42 |
| 7,713,487 B1 * | 5/2010 | Locklear et al. | 422/501 |
| 2003/0129094 A1 * | 7/2003 | Schubert et al. | 422/100 |
| 2002/0253195 | 10/2009 | Potts et al. | |

* cited by examiner

*Primary Examiner* — Jill Warden
*Assistant Examiner* — Brittany Fisher
(74) *Attorney, Agent, or Firm* — Daniel P. Burke & Associates, PLLC (57) ABSTRACT

Automated apparatus and methods for dispensing fluids into microplates utilizing microwell covers, the covers comprising open portions to allow a pipette access to one or more wells and impermeable portions which prevent the fluids from getting into wells shielded by the impermeable portion. The open portions and impermeable portions are preferably arranged and sized to align with alternating rows of wells in a particular microplate. Preferred covers are movably positioned on the microplate. Automated dispensing apparatus for use with microplates and microwell covers comprises a programmable controller, and suitable interfaces which allow the apparatus to be programmed, and which control a dispensing head such that pipettes are moved in the desired manner in order to take advantage of the protective features of the microwell covers. The apparatus also preferably comprises at least one transfer mechanism for moving a cover relative to a microplate at a dispensing station.

19 Claims, 12 Drawing Sheets

METHODS FOR DISPENSING FLUIDS INTO MICROPLATES UTILIZING MICROWELL COVERS

The present invention is directed to microwell covers for use with microplates used in laboratory testing, automated devices programmed to dispense fluid into a microplate using a microwell cover, and methods for dispensing fluids into a microplate.

BACKGROUND

Microplates, also known as microwell plates and microtitre plates, are a standard product and are regularly used in medical, chemical, and biological laboratories. Microplates have a plurality of sample wells typically arranged in a 2:3 rectangular matrix. For example, a common configuration for a microplate has 96 wells arranged in an 8×12 matrix.

In the laboratory, microplates are commonly supplied with various liquids, e.g. samples, reagents, and solvents. The particular liquids used will depend on the test being performed. During use, it is important to the accuracy of the laboratory procedure being performed that each liquid be dispensed into the desired well without cross contamination or unintended dispensing of a liquid into the wrong well. It is also important to the efficient operation of a laboratory to be able to dispense liquids into the desired sample wells accurately and rapidly. Therefore, automated machines have been introduced for automatically dispensing desired liquids into designated wells of a microplate. Whether a liquid is dispensed into a sample well or drawn from a well, and whether dispensed manually or using an automated apparatus, the liquid is typically moved with some type of pipette.

Some laboratory procedures utilize two types of microplates, namely, filter plates and collection plates. As these terms are used herein, filter plates have wells, sometimes referred to as columns, with openings at both the top and bottom, whereas collection plates have openings at the top but are closed at the bottom. As used herein, the term "well" is used to indicate a well of a microplate having either an open bottom (sometimes referred to as a column) or a closed bottom as in a collection plate. During common procedures, an adsorbent packing material is provided in each well of a filter plate. After the sample fluid has been placed into the well, the adsorbent is washed with suitable solvents to remove unwanted compounds which are directed to a waste station. Then the filter plate is placed over a collection plate and the desired analyte is removed from the packing material using a suitable eluent and the eluate is collected in the collection plate.

When liquids are moved to any of the wells in a microplate other than the wells located on the outer perimeter of the microplate, it is necessary to move the pipette containing a liquid over wells other than the well to which the liquid is intended. This creates a risk of unintended contamination by a liquid entering a well for which it is not intended.

SUMMARY OF THE INVENTION

Various embodiments of the present invention comprise microwell covers for microplates. The covers comprise open portions to allow a pipette access to one or more wells and impermeable portions which prevent the liquids from getting into wells shielded by the impermeable portion. As described in further detail below, preferred embodiments comprise impermeable portions with receptacles for catching any errant liquids and open portions with discrete openings sized and configured so that a discrete opening is provided in the cover for each well in a row of a microplate. The open portions and impermeable portions are preferably arranged and sized to align with alternating rows of wells in the particular microplate with which the cover will be used. Preferred covers are designed to be movably positioned on the microplate, for example, by sliding the cover along the top of the microplate in order to reposition the impermeable portions and open portions of a cover over different wells in the microplate, preferably over different rows of wells.

Other embodiments comprise automated dispensing apparatus, microplates, and microwell covers. The automated dispensing apparatus comprises a programmable controller, such as a microprocessor, and suitable interfaces, either onboard or external such as a laptop or personal computer, which allow the apparatus to be programmed and which control a dispensing head such that pipettes are moved in the desired manner in order to take advantage of the protective features of the microwell covers. The apparatus also preferably comprises at least one transfer mechanism for moving a cover relative to a microplate at a dispensing station and/or moving microplates and microwell covers from their respective supply positions according to preprogrammed instructions.

Other embodiments comprise methods for dispensing fluids to wells in a microplate. One such method comprises providing a liquid dispenser, a microplate, and a microwell cover; aligning an open portion of the cover with at least one row of wells; dispensing at least one liquid into a first well; subsequently moving the microwell cover relative to the microplate so that the open portion is aligned with a different row of wells; and subsequently dispensing at least one liquid into a least one second well by passing the liquid through an open portion of the microwell cover.

Another method comprises providing a liquid dispenser, a microplate, and a microwell cover; moving the dispenser to a position over an impermeable portion of the cover and subsequently to a position over an open portion; dispensing a liquid into a well by passing liquid through an open portion of the cover; subsequently moving the dispenser over an impermeable portion; and subsequently moving the dispenser from a position over an impermeable portion to a position which is not over the microplate.

These and other aspects are described in further detail below.

DETAILED DESCRIPTION

One aspect of the present invention comprises a microplate, a microwell cover configured for use with the microplate, and an automated laboratory apparatus comprising liquid dispensing and microplate transfer mechanisms. The automated laboratory apparatus has the ability to dispense liquids to at least one and preferably a plurality of wells/columns in a microplate through one or more dispensing tips. As used herein, the term "dispensing tips" includes reusable and disposable pipettes, as well as other liquid dispensers suitable for dispensing a liquid into a specific well of a microplate. The dispensing tip is alternatively, releasably attachable or integrally formed with the automated apparatus. In the case of a disposable pipette, the disposable pipette is releasably connectable to a dispensing head. Preferred embodiments utilize a plurality of releasably attachable dispensing tips in the form of pipettes, for example, 48 pipettes arranged in 6 rows of 8 pipettes in each row.

In use, the cover is positioned on top of the microplate which typically comprises a matrix of wells. Commonly used microplates have wells arranged in a 2:3 rectangular matrix, for example an 8×12 matrix totaling 96 wells. The present invention is useful with microplates having different numbers of wells and different configurations but is illustrated and explained herein with reference to 96 well microplates for purposes of illustration.

Figure 1:
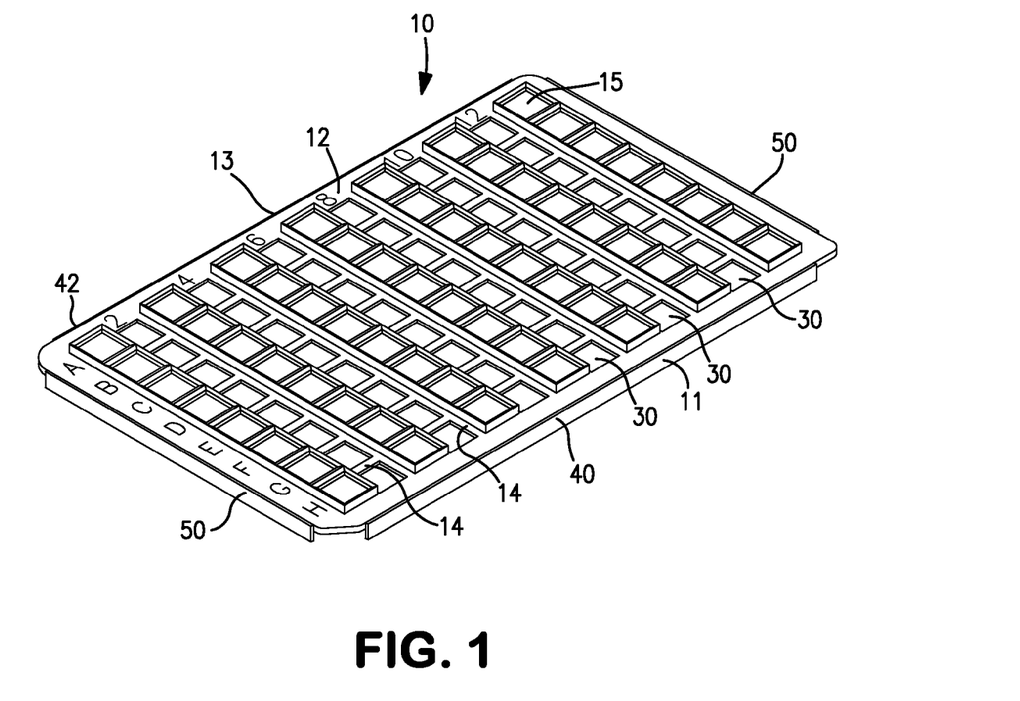
FIG. 1 is a top perspective view of one type of microwell cover of the present invention.

FIG. 1 is illustrative of one type of microwell cover of the present invention designed for use with a 96 well microplate. The illustrated microwell cover 10 has a generally rectangular configuration designed to rest on a generally rectangular microplate. Cover 10 comprises a frame 12, seven rows of receptacles 15 extending generally from the front portion 11 of the cover to the rear portion 13. The eight receptacles in each row are configured to align with eight wells in a row of the microplate. Between each row of receptacles 15 is a row of eight discrete openings 30 for a total of six rows of openings. The openings 30 in the peripheral row of openings 30 are defined by the frame 12 and both laterally and longitudinally extending spacers 14. The other openings 30 of this embodiment are defined by four laterally and longitudinally extending spacers 14.

Figure 6:
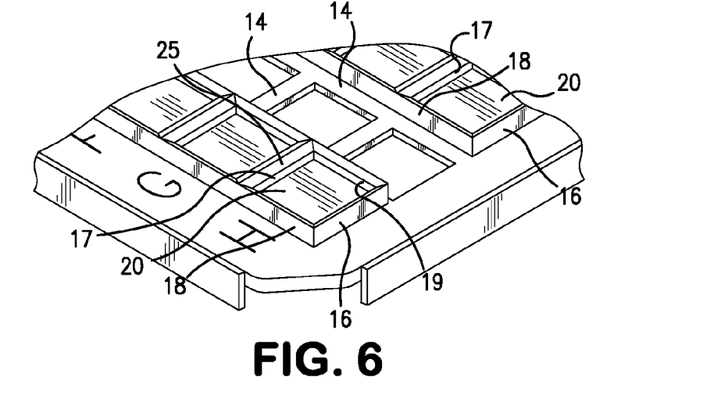
FIG. 6 is a close up perspective view of a portion of the cover shown in FIG. 1.

As best shown in the close-up view of FIG. 6, in this preferred embodiment, receptacles 15 are defined by an upwardly extending forward wall 16, rearward wall 17, left wall 18, right wall 19, and a solid bottom surface 20. Receptacles 15 are designed to catch liquid which inadvertently drips from a pipette as the pipette is moving to or from its intended position over a predetermined well of a microplate. While other configurations can be used, it is preferable to have the tops of the walls separating the receptacles formed as inclined surfaces without much of a horizontal surface in order to direct any errant droplets into receptacle 15. FIG. 6 illustrates an inclined surface 25 formed on the upper regions of each of walls 16-19.

Figure 2:
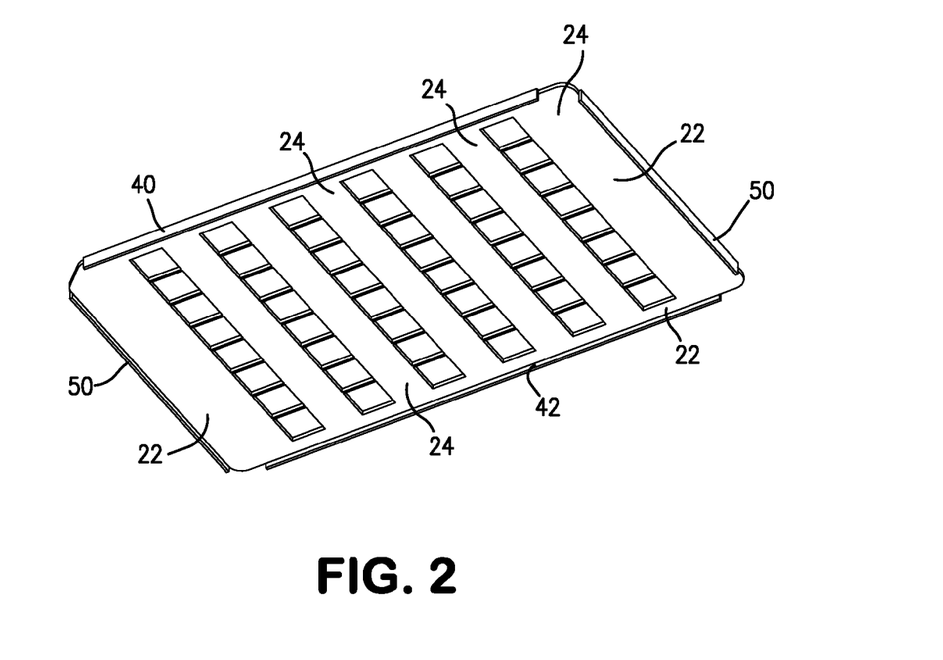
FIG. 2 is a bottom perspective view of the cover shown in FIG. 1.
Figure 4:
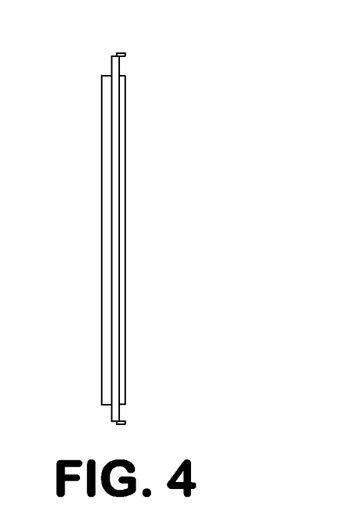
FIG. 4 is a right side view of the cover shown in FIG. 1.

As best illustrated in the bottom view of FIG. 2 and the side view of FIG. 4, the bottom surface 22 of frame 12 and the downwardly facing surfaces 24 located below receptacles 15 are generally co-planar in this illustrated embodiment. It is also feasible to have surfaces 24 positioned higher then bottom surfaces 22 of frame 12. In either configuration it is preferred that the bottom portions of receptacles 15 do not extend below the bottom surface 24 of frame 12. This facilitates the sliding movement of cover 10 across the top of a microplate as described further below.

Illustrated cover 10 also comprises longitudinally extending front rail 40 and rear rail 42 which extend downwardly below the lower surface of frame 12. Rails 40, 42 help to maintain the proper orientation of cover 10 when it is positioned on a microplate. Cover 10 also comprises right and left stops 50 which extend downwardly from frame 12 at the left and right portions of cover 10. Stops 50 are positioned relative to frame 12 such that when stops 50 are positioned in abutment with a left or right edge of a microplate, rows of receptacles 15 and rows of openings 30 are aligned over different rows of wells of a microplate.

Figure 3:
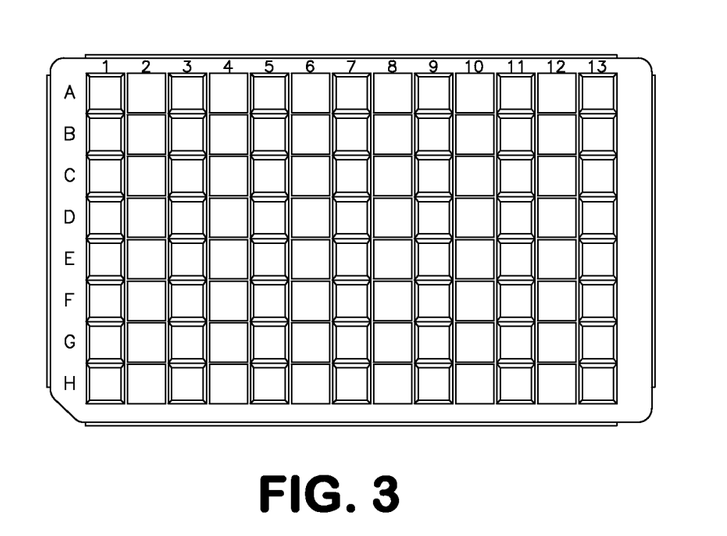
FIG. 3 is a top view of the cover shown in FIG. 1.
Figure 5:
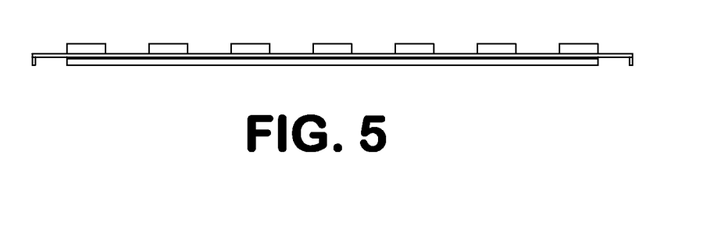
FIG. 5 is a front view of the cover shown in FIG. 1.

FIG. 3 is a top view of microwell cover 10 shown in FIG. 1. For purposes of reference, each column has been numbered 1-13 and each row is designated with the letters A-H. FIG. 4 is a right side view of the microwell shown in FIG. 3, while FIG. 5 is a front view of the cover 10 shown in FIG. 3.

From the present descriptions and drawings it will be appreciated that illustrated cover 10 comprises one more row of total receptacles and openings than the total number of rows of wells in the illustrated microplate. For example, a standard 96 well microplate comprises twelve laterally extending rows of wells each comprising eight wells. Illustrated cover 10 which is designed for use with a standard 96 well plate comprises a total of thirteen rows, including seven rows of receptacles and six rows of openings. This allows cover 10 to be moved laterally along the top of a 96 well microplate during a laboratory procedure in order to provide access to a first half of the wells while shielding a second half of the wells when the cover is in one position. After the cover 10 has been moved, the first half of the wells are shielded and the second half are accessible. The wells which are not accessible at any given time are shielded by receptacles which form an impermeable barrier to errant liquids which might otherwise travel into an incorrect well. It will be appreciated that frame 12 also provides some protection against airborne droplets which might otherwise enter an incorrect well. According to this illustrated embodiment of the cover, all wells of the microplate are accessible to pipetting during the course of a laboratory procedure, but all of the wells are not accessible at the same time.

Figure 7:
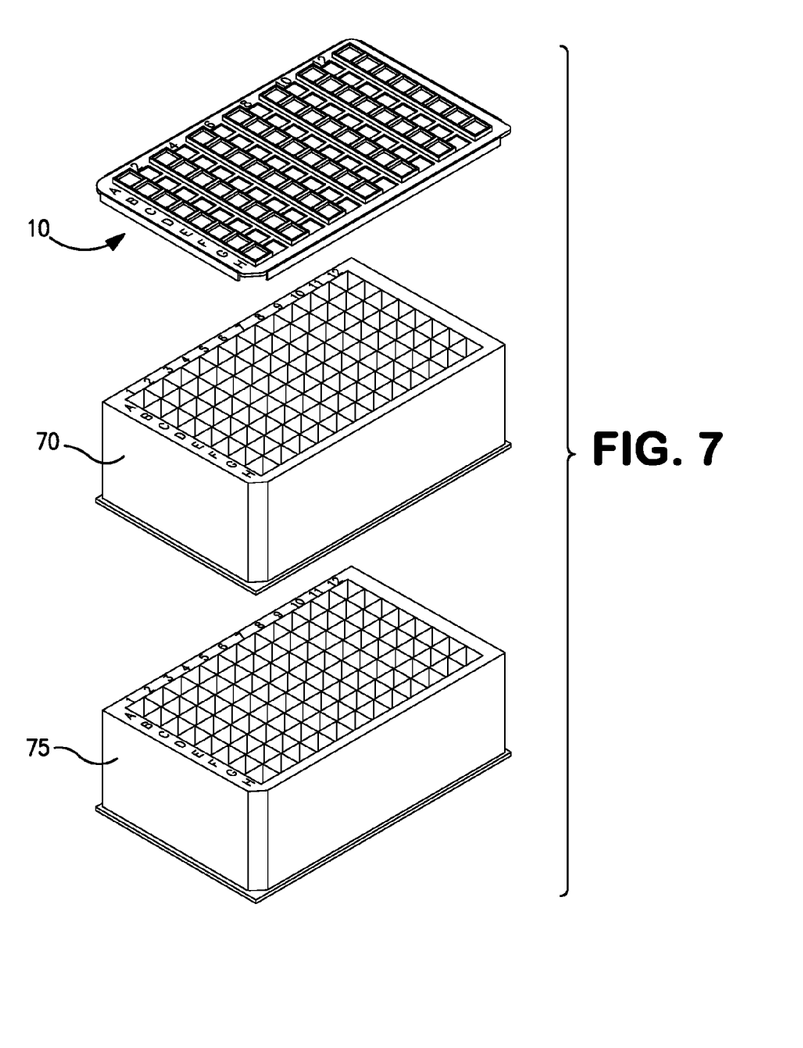
FIG. 7 is an exploded perspective view of the cover shown in FIG. 1, a filter plate and a collection plate.

FIG. 7 is an exploded view of a microwell cover of the present invention positioned above a filter plate 70 which is positioned above a collection plate 75. From the present description those skilled in the art will appreciate that during a collection step, the filter plate 70 is positioned on top of the collection plate 75 while the cover 10 is positioned on top of filter plate 70.

Figure 8:
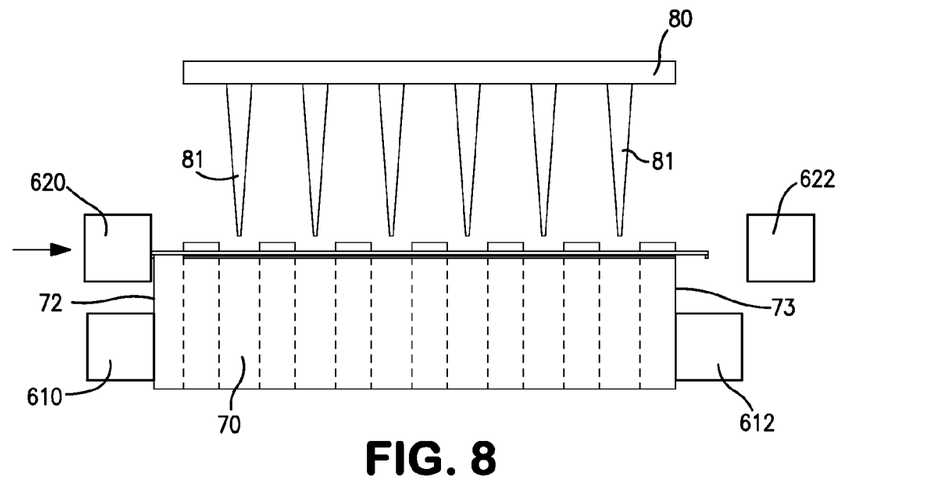
FIG. 8 is a side view of the cover of FIG. 1 on a filter plate in a first position.
Figure 9:
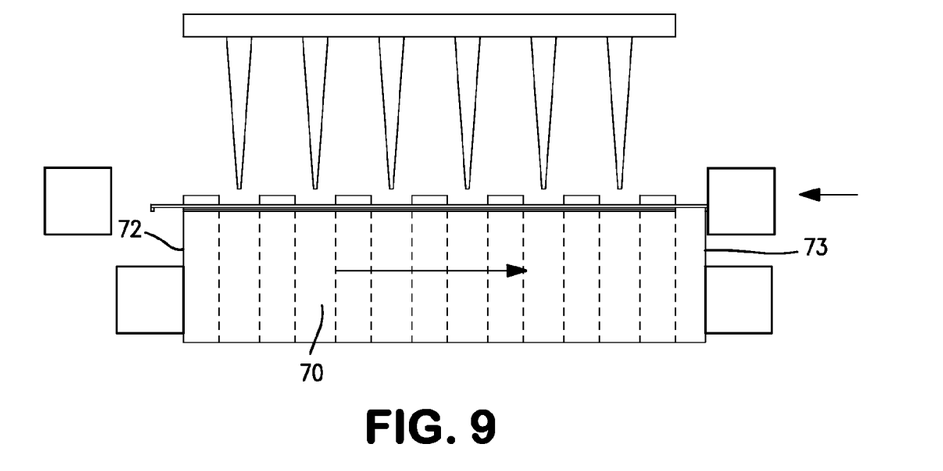
FIG. 9 is a side view of the cover of FIG. 1 on a filter plate in a second position.

FIGS. 8 and 9 illustrate microwell cover 10 positioned on a deep well collection plate 70. In FIG. 8, cover 10 is positioned with left stop 50 abutting left edge 72 of the microplate 70 thereby aligning openings 30 with the even number rows of wells in microplate 70, namely rows 2, 4, 6, 8, 10 and 12. In this position, the receptacles of cover 10 shield the wells in the odd numbered rows, namely rows 1, 3, 5, 7, 9 and 11. Thus, when cover 10 is in this position, liquid can be dispensed by dispenser 80 through pipettes 81 into the wells in the accessible even numbered rows, while reducing the risk of accidentally dripping liquid into the odd numbered rows.

FIG. 9 illustrates cover 10 positioned with right stop 50 abutting the right edge 73 of microplate 70 in order to align openings 30 with the odd number rows of wells in microplate 70, namely rows 1, 3, 5, 7, 9 and 11. Thus it will be appreciated that by moving cover 10 relative to microplate 70, half of the wells of the microplate can be made accessible to pipettes for the dispensing of fluid or for drawing fluid from wells of microplate 70 while the other half of the wells are shielded by the impermeable portions of cover 10 comprising receptacles 15.

FIGS. 8 and 9 also illustrate the fingers of a transfer mechanism which move covers relative to a microplate, and preferably also transfer microplates and microwell covers from supply stations to a dispensing station and then to a disposal station. In FIG. 8, lower fingers 610 and 612 hold microplate 70 in a stationary position while left upper finger 620 has moved cover 10 to the right until the left stop 50 engages the left side 72 of microplate 70 in order to properly align the openings and impermeable portions of cover 10 with the desired wells of microplate 70. In FIG. 9, lower transfer fingers 610 and 612 continue to hold microplate 70 in a stationary position while right upper finger 622 has moved cover 10 to the left until right stop 50 has abutted the right side 73 of microplate 70.

FIGS. 10-18 illustrate advantages of the present invention as well as methods for distributing liquids to wells in a microplate. This embodiment utilizes an automated apparatus comprising a liquid dispenser 80 designed to pick up disposable pipettes 81 from a pipette supply rack, draw a predetermined liquid into each pipette wherein each liquid is to be dispensed into a predetermined specific well, and then to move the pipettes such that the pipettes do not pass over any open wells before arriving at the well to which the particular liquid in each pipette is intended.

Figure 10:
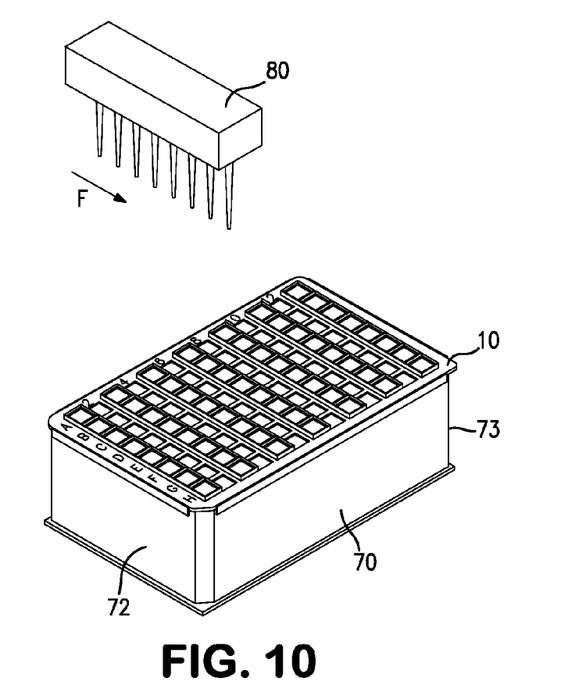
FIGS. 10-18 illustrate one method of the present invention.

In FIG. 10 an exemplary liquid dispenser 80 starts from a position which is not over cover 10 or microplate 70. The dispenser head had previously been moved over a pipette supply rack and lowered into engagement with eight pipettes which are temporarily secured to the dispensing head. The dispensing head is then moved over at least one liquid supply container where the dispensing head draws a desired liquid into each pipette. The pipettes can be each supplied with a different liquid, or one or more of the pipettes can be supplied with the same liquid. As shown in FIG. 10, the dispensing head is then moved to a position which is higher than and in alignment with an impermeable portion of cover 10 which is blocking liquid access to the wells in row 12. In this position, the dispenser 80 is not positioned over either the cover 10 or the microplate 70. In FIGS. 10-18, cover 10 is positioned to the left so that odd numbered rows of wells in microplate 70 are accessible while even numbered rows of wells are shielded by the impermeable portions of cover 10.

Figure 11:
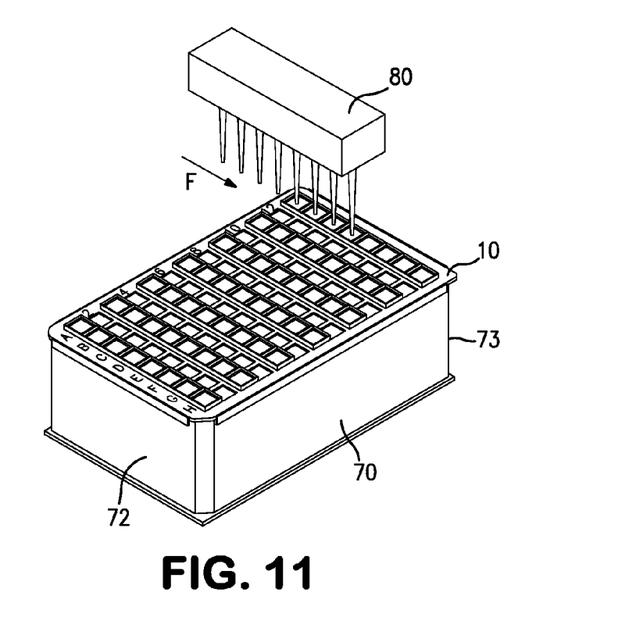
Figure 12:
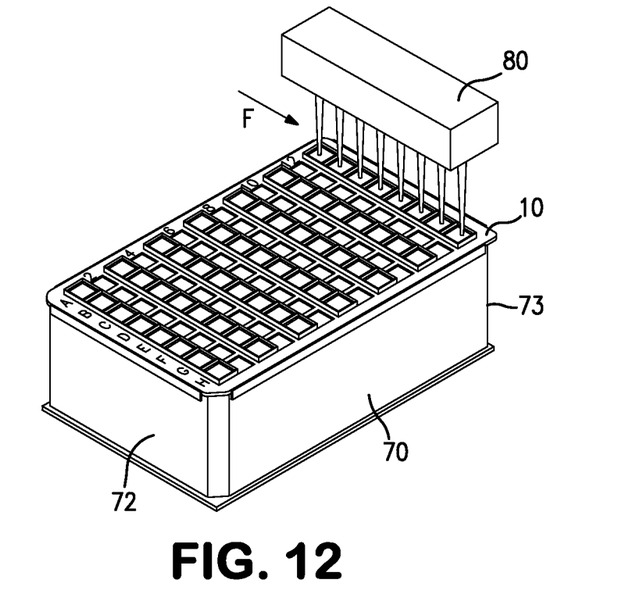
Figure 13:
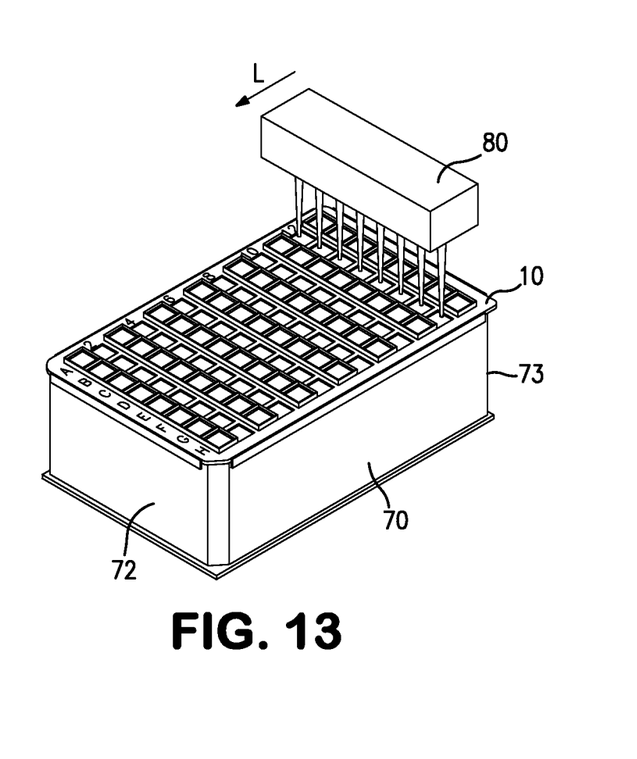
Figure 14:
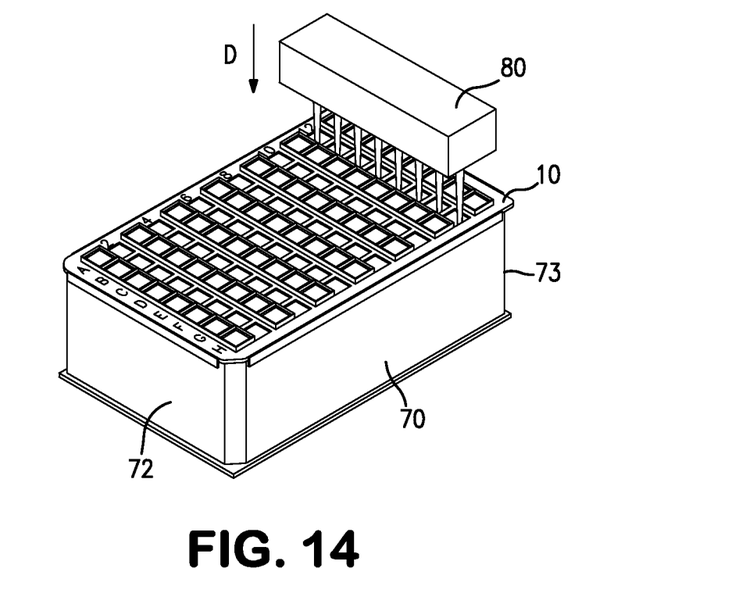
Figure 15:
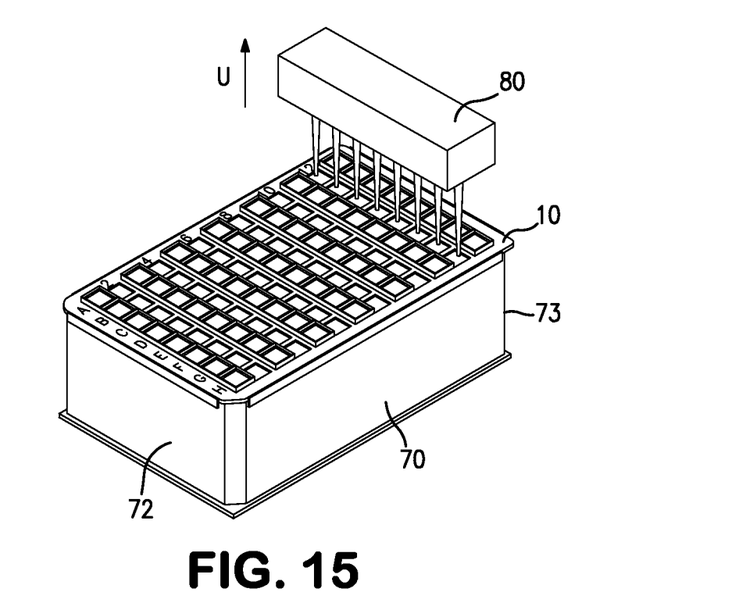
Figure 16:
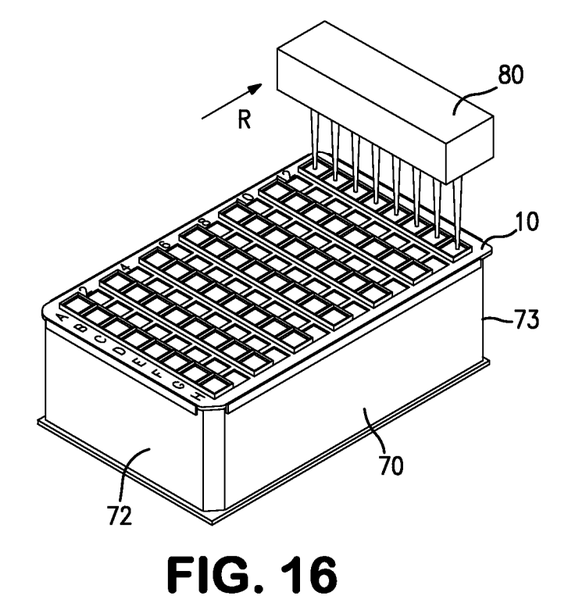
Figure 17:
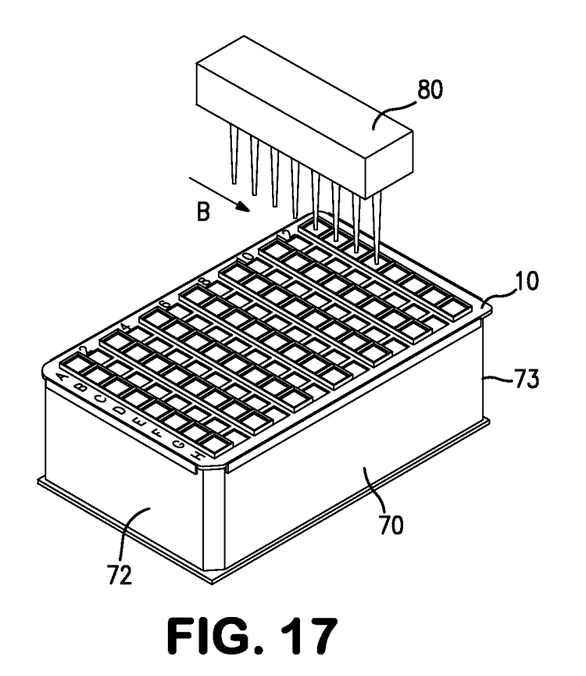
Figure 18:
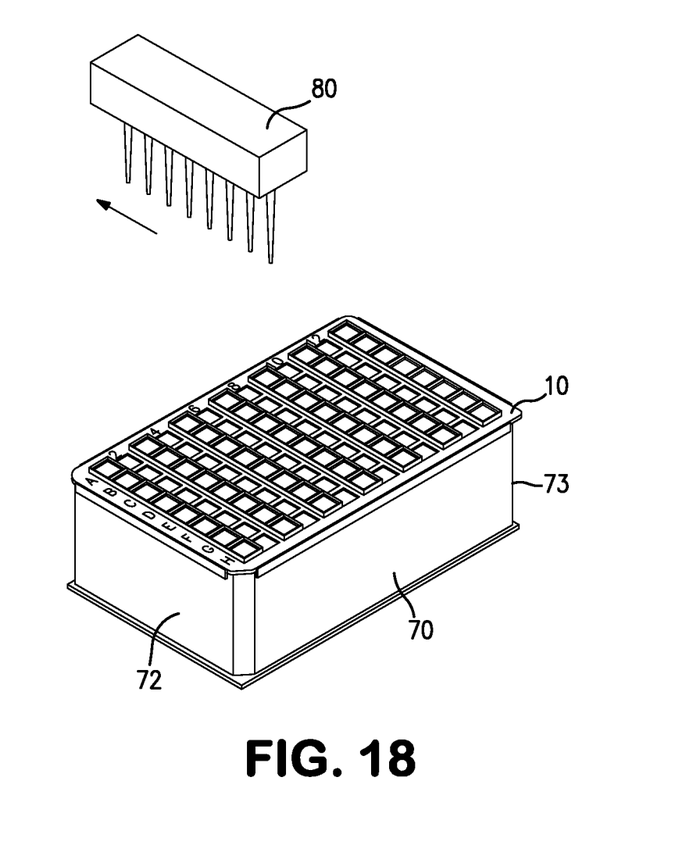

At a desired time, dispenser 80 is moved forwardly in the direction of arrow F while maintaining the pipettes over receptacles 15 as shown in FIG. 11. With reference to FIG. 12, the dispensing head 80 continues in the direction of arrow F to move the pipettes 81 until each pipette is positioned over a receptacle 15 and in lateral alignment with a desired opening 30 of row 11 in microplate 70. With reference to FIG. 13, dispensing head 80 is then moved to the left in the direction of arrow L to position each pipette over an opening 30 of row 12 in cover 10 (which is aligned with the wells in row 11 of the microplate 70). In the position shown in FIG. 13, the pipettes are disposed directly over wells in row 11 of microplate 70. If desired, the dispensing head 80 is then lowered in the direction of arrow D as shown in FIG. 14 causing the pipettes and any liquid contained in the pipettes to move through the openings of cover 10 and into the desired wells of row 11 where the liquid is then dispensed. With reference to FIG. 15, the dispensing head 80 is then raised upwardly in the direction of arrow U to a height which is higher than the receptacle sidewalls. As shown in FIG. 16, the dispensing head is then moved to the right in the direction of arrow R in order to position all of the pipettes over receptacles 15. As shown in FIG. 17, the dispensing head 80 is then moved in the direction of arrow B while keeping the pipettes over receptacles 15 in order to move the dispensing head 80 to a position where it is no longer positioned over the microplate 70 or cover 10 as shown in FIG. 18.

From the present description it will be appreciated that during this method each pipette was never positioned over an unshielded well other than the well for which the liquid in that specific well was intended. In this manner, the microwell cover and manner of positioning pipettes over a microplate greatly minimize any chance of contamination from an errant liquid passing into an unintended well.

It will also be appreciated that the advantages of the present invention and the minimization of cross contamination are achieved whether the pipettes are dispensing liquid into the wells or drawing liquid from wells such as the wells of a collection plate. In the case of drawing liquid from wells in a collection plate, the path of the dispensing head is similar except for the elimination of the step of drawing fluid into the pipettes which is performed when the pipettes are in the position shown in FIG. 14 rather than when in the position prior to that shown in FIG. 10.

As an alternative to the path of the dispenser 80 shown in FIGS. 10-18, after the dispensing head 80 has dispensed fluid into the open wells, instead of moving the dispensing head to the right (to a position over shielded portions of the cover) and then moving it to a position which is not over the cover and microplate, after the dispensing head has dispensed liquid and been raised out of the wells to the position shown in FIG. 15, the head can be moved to the left for a distance of two rows to dispense fluid into the wells of row nine and can optionally continue in this manner dispensing liquid through each of the open portions into wells in microplate 70.

Dispensing head 80 is shown as supporting a single row of eight pipettes for clarity of illustration but more preferably, a dispensing head for the microplate shown in FIGS. 10-18 would comprise six rows of pipettes with each row having eight pipettes. In such a configuration, all open wells would be supplied with a desired fluid when the pipettes are in the position illustrated in FIG. 14.

Figure 19:
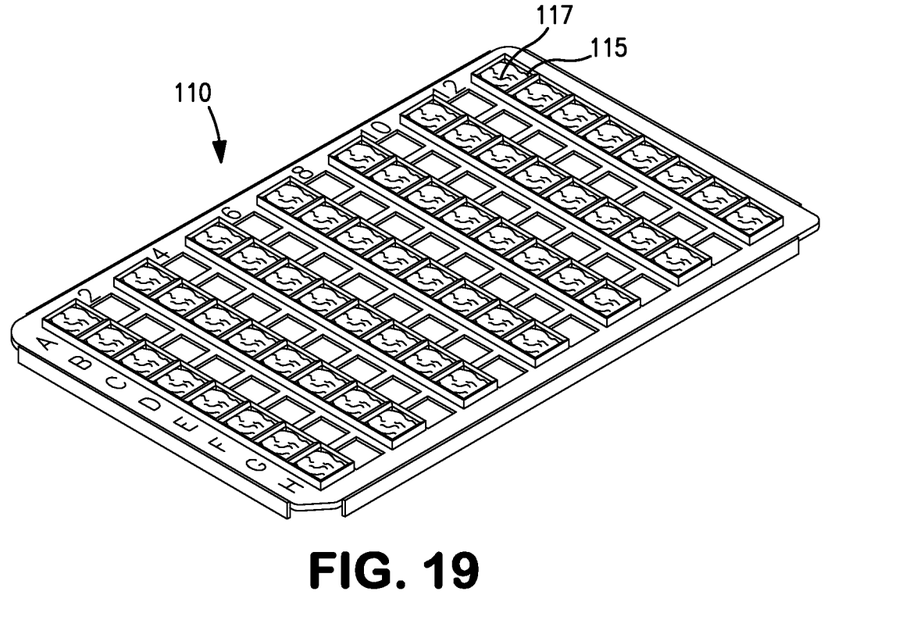
FIG. 19 illustrates a microwell cover of an alternative embodiment of the present invention.
Figure 20:
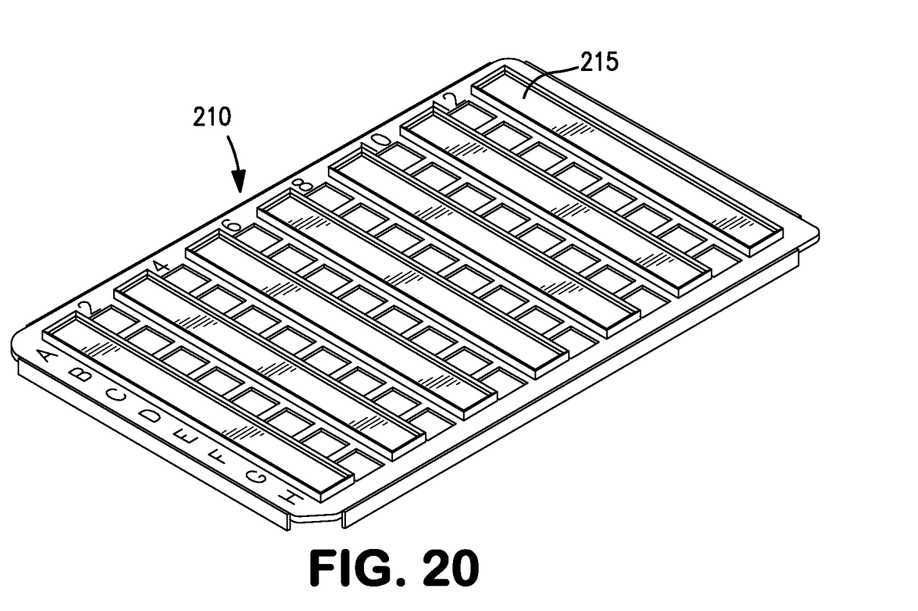
FIG. 20 illustrates a microwell cover of a third embodiment of the present invention.

While the configuration of the cover 10 shown in FIGS. 1-7 is presently preferred, other configurations of covers may be used. FIG. 19 illustrates an alternative cover of the present invention which is similar to cover 10 shown in FIG. 1 but further comprises an absorbent material 117, such as absorbent paper, cotton, a non-woven material, etc. in each receptacle 115. FIG. 20 illustrates a still further embodiment of the present invention which is also similar to the embodiment shown in FIGS. 1-7 however in this embodiment the impermeable portions of cover 210 comprise continuous troughs 215 which extend for the full length of a row. The side rows defining each trough 215 preferably comprise tapered edges similar to tapered edges 25 shown in FIG. 6.

Figure 21:
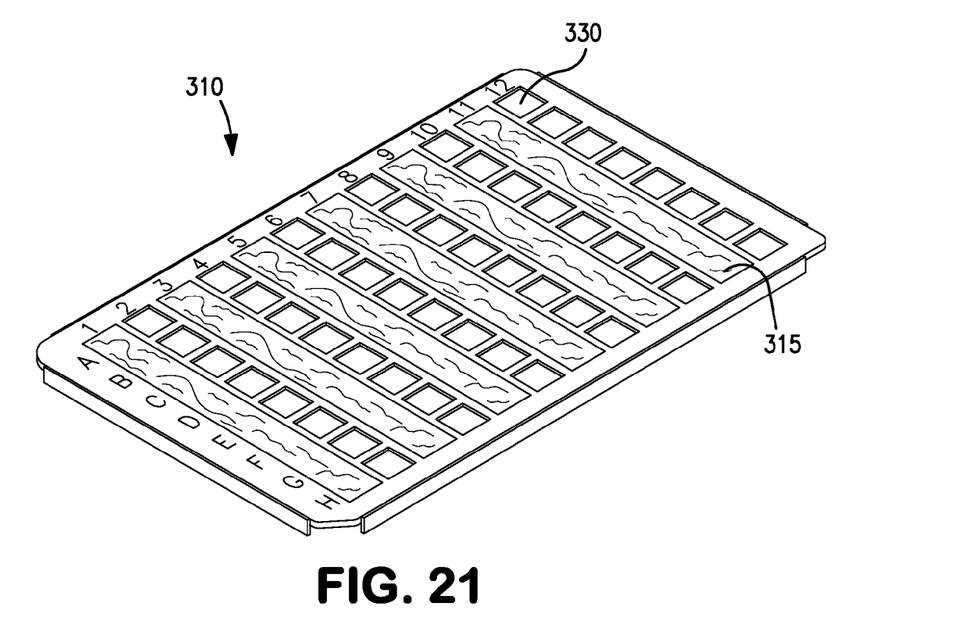
FIG. 21 illustrates a microwell cover of a fourth embodiment of the present invention.

FIG. 21 illustrates a still further embodiment of the present invention comprising cover 310. Cover 310 comprises a total of 12 rows of openings and impermeable portions, i.e. the same number of rows as the microplate for which cover 310 is intended to be used. In this illustrated embodiment, the impermeable portions comprise strips of absorbent paper 315 which are secured between the rows of openings 330. Alternatively, other absorbent or adsorbent materials can be used. According to this embodiment, rather than simply sliding cover 310 to change the wells to which a pipette has access, the cover is rotated 180$^N$ relative to the microplate.

Figure 22:
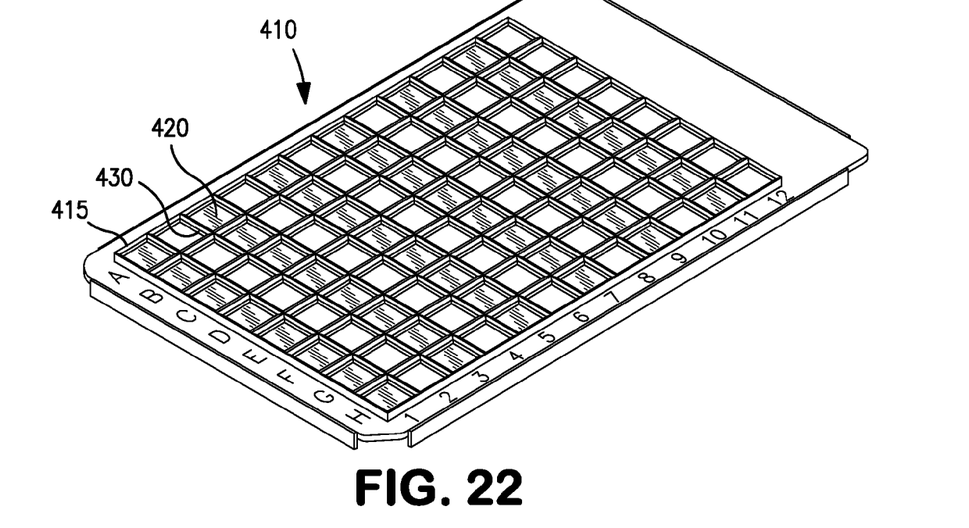
FIG. 22 illustrates a microwell cover of a fifth embodiment of the present invention.

FIG. 22 illustrates a still further embodiment of the present invention wherein both the impermeable portions and portions with openings comprise walls to separate adjacent portions. The cover 410 shown in FIG. 22 comprises rows of receptacles 415 having closed bottom surfaces 420 while adjacent rows of open portions comprise side walls with open bottoms 430. Closed bottoms 420 in each of the impermeable sections, namely the odd numbered rows 1, 3, 5, 7, 9 and 11 are indicated with shading while the even numbered rows have openings to allow liquid access to wells aligned with those openings. This embodiment also comprises an equal number of rows of openings and impermeable receptacles but is wide enough for cover 410 to be moved laterally in the manner illustrated in FIGS. 8 and 9 in order to align openings and shielded areas with different rows of microwells when desired.

The covers are preferably formed of materials which will have sufficient durability during their expected life span in the environments in which they will be used, including contact with the fluids used during various procedures. For example, suitable materials for most applications include polyethylene, polypropylene and Teflon®.

Figure 23:
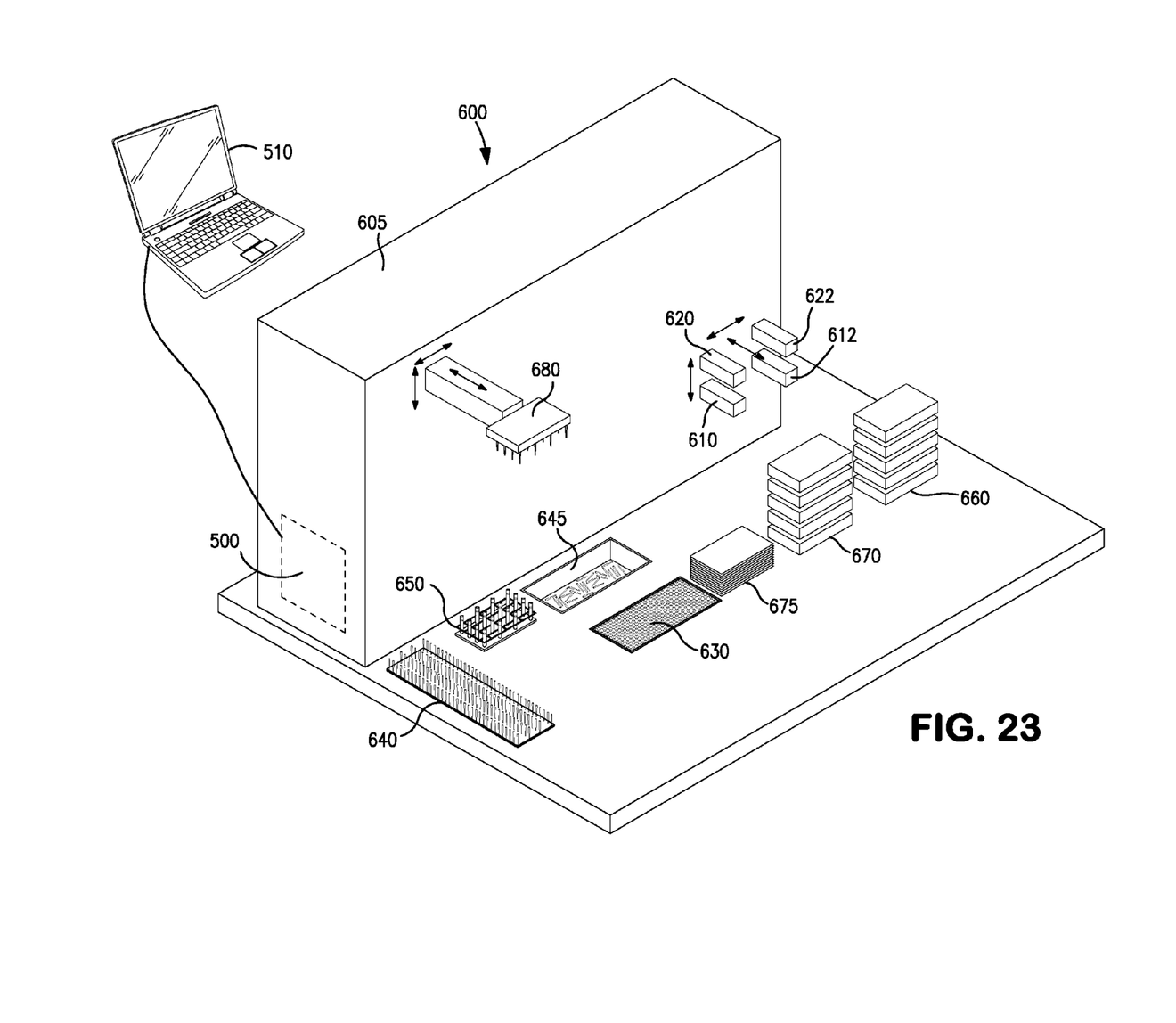
FIG. 23 diagrammatically illustrates an automated dispensing apparatus for performing methods of the present invention.

While the covers of the present invention and the methods described can be utilized when liquid is manually dispensed into a microplate, it is preferable to use an automated laboratory apparatus to increase speed, accuracy and efficiency of a laboratory processing multiple samples. FIG. 23 diagrammatically illustrates a automatic laboratory apparatus 600 comprising a housing 605 and a dispensing head 680 supported by a dispensing arm 685 which is movable horizontally, vertically, and into and out of housing 605 as indicated by the arrows in FIG. 23. Apparatus 600 also comprises a transfer mechanism comprising lower fingers 610, 612 and upper fingers 620, 622. Each of the fingers of the transfer mechanism can preferably be moved independently of each other as well as horizontally, vertically and into and out of housing 605. A programmable controller 500, linked to a suitable input device 510 such as a computer or touch screen, is used to control the operation and movement of dispensing head 680 and fingers 610, 612, 620 and 622.

This illustrated embodiment comprises a dispensing station 630, a pipette supply station 640, a liquid supply station 650, a pipette disposal area 645, a filter plate supply 660, a collection plate supply 670 and a microwell cover supply 675.

Controller 500 is programmable to cause transfer mechanism, preferably lower fingers 610 and 612 to initially move a filter plate from filter plate supply 670 to dispensing station 630, then a cover from cover supply 675 is retrieved by upper fingers 620, 622 and positioned on top of a filter plate at the dispensing station 630. Simultaneously or sequentially with the transfer of the filter plate and cover to dispensing station 630, dispensing head 680 picks up pipettes from pipette supply 640 and draws the desired liquid into those pipettes at liquid supply station 650. Dispensing head 680 then moves the pipettes to the desired wells, preferably in the manner described above with respect to FIGS. 10-18. After liquid has been dispensed into some of the wells in a microplate, the cover is moved relative to the microplate by the transfer fingers in the manner illustrated above in FIGS. 8 and 9. Namely, lower fingers 610, 612 can grasp the filter plate and hold it in place while at least one of upper fingers 620, 622 moves the cover relative to the microplate in order to align the openings of the cover with different columns in the microplate. Alternatively, the cover is kept in place and the plate is moved, or both are moved in opposite directions. After liquid has been dispensed as desired and dispensing head 680 is moved to a position where it is no longer positioned over dispensing station 630, the pipettes are ejected into pipette disposal container 645. When it is desired to collect sample from a filter plate, transfer arms can be used to position a collection plate under the filter plate.

Thus the automated laboratory apparatus is preferably designed to retrieve microplates and covers from respective supply racks, position the cover on a microplate in a desired position, move the cover relative to the microplate when desired and remove the cover from the microplate after the desired dispensing and/or withdrawing of fluids has occurred. The automated apparatus also moves each dispensing tip, e.g. pipette, in a manner such that the dispensing tips are moved over shielded portions until arriving at the opening aligned with the well to which the liquid in a given dispensing tip is intended to be dispensed.

The invention claimed is:

1. A method for dispensing fluid into a microplate comprising the steps of:
   providing a microplate comprising a plurality of wells;
   providing a microwell cover comprising:
      a plurality of impermeable portions, each of said impermeable portions configured to shield a plurality of shielded wells; and
      a plurality of open portions, each of said open portions configured to be aligned above a plurality of accessible wells while permitting fluid access to said plurality of accessible wells;
      each of said impermeable portions disposed between different open portions;
   aligning said open portions with a plurality of originally accessible wells;
   dispensing fluid into at least one of said originally accessible wells in each of a plurality of rows by passing fluid through open portions corresponding to said originally accessible wells to which fluid is dispensed;
   subsequently moving said microwell cover relative to said microplate so that said open portions are aligned with different pluralities of newly accessible wells; and
   subsequently dispensing at least one fluid into at least one newly accessible well by passing said fluid through an open portion of a said microwell cover, wherein said newly accessible well was not an originally accessible well.

2. A method for dispensing fluid into a microplate according to claim 1 wherein said step of providing a microplate comprising a plurality of wells comprises providing a microplate comprising a plurality of wells arranged in a rectangular matrix.

3. A method for dispensing fluid into a microplate according to claim 1 wherein said aligning step comprises aligning an impermeable portion with an originally accessible well.

4. A method for dispensing fluid into a microplate according to claim 1 wherein said step of providing a microplate comprises providing a microplate comprising a plurality of wells arranged in a plurality of rows and said step of providing a microwell cover comprises providing alternating impermeable portions and open portions configured for alignment with adjacent rows of wells.

5. A method for dispensing fluid into a microplate according to claim 4 wherein said aligning step comprises aligning an impermeable portion with a row of wells.

6. A method for dispensing fluid into a microplate according to claim 4 wherein said dispensing step comprises simultaneously dispensing liquids into a plurality of wells located in a plurality of non-adjacent rows.

7. A method for dispensing fluid into a microplate according to claim 1 wherein said step of providing a microwell cover comprises providing a cover with n open portions and n+1 impermeable portions.

8. A method for dispensing fluid into a microplate according to claim 4 wherein said step of subsequently moving said microwell cover comprises moving said cover so that said open portions are aligned with rows of newly accessible wells which are adjacent to said originally accessible rows.

9. A method for dispensing fluid into a microplate according to claim 1 wherein said fluid is a liquid.

10. A method for dispensing fluid into a microplate comprising the steps of:
  providing a fluid dispenser comprising at least one dispensing tip;
  providing a microplate comprising a plurality of wells;
  providing a microwell cover comprising:
    a plurality of impermeable portions, each of said impermeable portions configured to shield a plurality of shielded wells; and
    a plurality of open portions, each of said open portions configured to be aligned above a plurality of accessible wells while permitting fluid access to said plurality of accessible wells;
      each of said impermeable portions disposed between different open portions;
  aligning said at least one open portion with at least one originally accessible well;
  moving said dispensing tip to a position over at least one impermeable portion;
  subsequently moving said dispensing tip to a position over an open portion;
  dispensing at least one fluid into at least one well by passing liquid through said open portion;
  subsequently moving said dispensing tip to a position over an impermeable portion; and
  subsequently moving said dispensing tip from a position over an impermeable portion to a position which is not over said microplate.

11. A method for dispensing fluid into a microplate according to claim 10 wherein said step of providing at least one dispensing tip comprises providing a pipette.

12. A method for dispensing fluid into a microplate according to claim 10 wherein said step of providing at least one dispensing tip comprises providing a plurality of pipettes arranged in a row.

13. A method for dispensing fluid into a microplate according to claim 10 wherein said step of providing a microplate comprises providing a microplate with a plurality of wells arranged in a rectangular matrix.

14. A method for dispensing fluid into a microplate according to claim 10 wherein said fluid is a liquid.

15. A method for dispensing fluid into a microplate according to claim 1 wherein said step of providing a microwell cover comprised providing a cover with alternating rows of impermeable portions and open portions.

16. A method for dispensing fluid into a microplate according to claim 10 wherein said step of providing a fluid dispenser comprises providing a fluid dispenser with a plurality of dispensing tips arranged in at least one row.

17. A method for dispensing fluid into a microplate according to claim 10 wherein said step of providing a microplate comprises providing a microplate comprising a plurality of wells arranged in a plurality of rows and said step of providing a fluid dispenser comprises providing a fluid dispenser with a plurality of dispensing tips arranged in a plurality of spaced rows configured for dispensing fluid into non-adjacent rows in said microplate.

18. A method for dispensing fluid into a microplate according to claim 1 wherein said step of providing a microwell cover comprising a plurality of open portions comprises providing at least one open portion comprising a plurality of openings separated by spacers.

19. A method for dispensing fluid into a microplate according to claim 10 wherein said step of providing a microwell cover comprising a plurality of open portions comprises providing at least one open portion comprising a plurality of openings separated by spacers.

\* \* \* \* \*